(12) United States Patent
Ozaki et al.

(10) Patent No.: US 8,491,490 B2
(45) Date of Patent: Jul. 23, 2013

(54) METHOD AND APPARATUS OF ANALYZING RESPIRATORY SIGNALS CORRESPONDING TO CHANGES IN SUBJECT'S LOADS APPLIED TO BED

(75) Inventors: Noriyuki Ozaki, Kariya (JP); Seiichi Yamada, Azumino (JP)

(73) Assignee: DENSO CORPORATION, Kariya (JP)

( * ) Notice: Subject to any disclaimer, the term of this patent is extended or adjusted under 35 U.S.C. 154(b) by 1723 days.

(21) Appl. No.: 11/648,893

(22) Filed: Jan. 3, 2007

(65) Prior Publication Data

US 2007/0161917 A1    Jul. 12, 2007

(30) Foreign Application Priority Data

Jan. 10, 2006   (JP) .................. 2006-002678

(51) Int. Cl.
*A61B 5/08* (2006.01)
(52) U.S. Cl.
USPC ........................................... 600/529

(58) Field of Classification Search
USPC ........................................... 600/529
See application file for complete search history.

(56) References Cited

U.S. PATENT DOCUMENTS 6,932,774 B2    8/2005   Nakatani et al.

*Primary Examiner* — Patricia Mallari
*Assistant Examiner* — Christian Jang
(74) *Attorney, Agent, or Firm* — Posz Law Group, PLC

(57) ABSTRACT

An analyzing apparatus comprises a first counter part and a second counter part. The first counter part determines a significant respiratory disorder pattern based on the average of multiple amplitudes included in a respiratory signal, and counts the number of respiratory disorders. The second counter part that determines, when the number of respiratory disorders per unit time counted by the first counter part is greater than a predetermined number, a significant respiratory disorder pattern by the values of individual amplitudes included in the respiratory signal, and again counts the number of respiratory disorders. A more accurate apnea hypopnea index is obtained for serious patients, and accuracy as PSG screening examination can be increased.

15 Claims, 4 Drawing Sheets

METHOD AND APPARATUS OF ANALYZING RESPIRATORY SIGNALS CORRESPONDING TO CHANGES IN SUBJECT'S LOADS APPLIED TO BED

CROSS REFERENCE TO RELATED APPLICATION

This application is based on and incorporates herein by reference Japanese Patent Application No. 2006-2678 filed on Jan. 10, 2006.

FIELD OF THE INVENTION

The present invention relates to a method and an apparatus of analyzing a respiratory signal obtained from a load signal corresponding to changes in a subject's loads applied to a bed, and more particularly to an analyzing method and apparatus for counting the number of respiratory disorders including apneas and hypopneas from the respiratory signal.

BACKGROUND OF THE INVENTION

It is disclosed in U.S. Pat. No. 6,932,774 (JP 2004-24684A) that changes in loads applied to a sleeper's bed are sensed by a sensor sheet having multiple pressure sensitive elements inserted in a lower portion of the bed. Furthermore, a method is disclosed which produces a respiratory body movement signal as a respiratory signal being a signal component of a frequency band corresponding to the number of sleeper's respirations from the load signal, and determines apnea states including an obstructive apnea state from a change pattern of amplitudes of the respiratory signal. In the obstructive apnea state in which a throat is blocked because of a throat muscle slacked by sleeping, and oxygen is not supplied to lungs, the sleeper performs respiratory operations, but oxygen is not supplied to the lungs because the throat is blocked. As a result, the oxygen saturation in blood decreases, and the sleeper temporarily falls into an awakened state and performs a very deep respiratory operation (labored respiration). As a result, the amplitudes of the respiratory signal increase suddenly. Therefore, by detecting the sudden or harp increase in amplitudes, an apnea state can be determined.

The sleep apnea syndrome includes obstructive apnea or central apnea that little oxygen is supplied to lungs, and hypopnea that oxygen supply is insufficient because a sleeper's respiratory tract is narrowed. Furthermore, since the frequency of the respiratory signal when the amplitudes increase becomes higher in comparison with the frequency of the respiratory signal when the amplitudes decrease, the amplitude decrease state of the respiratory signal is determined to be a sleeper's apnea state or hypopnea state.

A respiratory signal obtained from a load signal may include various noises. An example is periodic limb movements (PLM). Therefore, the average of multiple amplitudes in a respiratory signal is calculated, and a change in amplitudes of the respiratory signal is determined from a difference between the averages, thereby eliminating single-shot noise components.

To determine the severity of the sleep apnea syndrome, Apnea Hypopnea Index (AHI) is used. The AHI indicates the total number of apneas and hypopneas per hour of sleeping. To measure the AHI, polysomnography (PSG) is used. The PSG records various physiological changes in electroencephalogram, electrooculogram, electrocardiogram, muscular movements, and the like throughout sleeping of one night, and analyzes the results, thereby evaluating the type and the severity of the sleep apnea syndrome. The examination by the PSG is considered to have high accuracy because it records various physiological changes. However, since the PSG requires that various sensors must be attached to a patient, a significant burden is placed on the sleeping patient. It is thus difficult to detect situations during natural sleeping. Furthermore, much time is required to analyze examination results, and high costs are required for the analysis.

In this regard, the above method of obtaining a respiratory signal by a load signal is simple, places little burden on a sleeping patient, enables detection of situations during natural sleeping, makes the analysis of examination result relatively easy, and is therefore inexpensive. Therefore, the apparatus and method of analyzing a respiratory signal are suitable as a measuring apparatus or a process for screening to determine whether a patient requires measurements by the PSG. Furthermore, application to an apparatus and a process of determining the severity of the sleep apnea syndrome is under consideration. However, to achieve the object, a further increase in the measurement accuracy of a measuring apparatus for screening is demanded. Furthermore, hereinafter, to differentiate from the AHI indicating measurement results of the PSG, an apnea hypopnea index measured by the present apparatus or method is described as pAHI. The pAHI indicates the number of apnea states or hypopnea states per hour.

SUMMARY OF THE INVENTION

The present invention has its object to increase accuracy of measurement in determining sleep apnea syndrome by measuring and analyzing a respiratory signal.

According to one aspect of the present invention, an analyzing method analyses a load signal obtained by changes in loads of a subject (person to be measured, such as a patient) applied to a bed. This analyzing method has a first step and a second step.

In the first step, the number of respiratory disorders, including apneas and hypopneas, are counted using a respiratory disorder pattern in which a signal of low amplitudes (signal of first amplitudes) is followed by a signal of high amplitudes (signal of second amplitudes), included in a respiratory signal extracted from the load signal. A significant respiratory disorder pattern is determined by averaged amplitude data corresponding to the average of multiple amplitudes included in the respiratory signal, and the number of respiratory disorders is counted.

In the second step, when the number of respiratory disorders per unit time counted in the above step is greater than a predetermined number, a significant respiratory disorder pattern is determined by individual amplitude data corresponding to the respective values of amplitudes included in the respiratory signal, and the number of respiratory disorders is counted again.

In patients having the apnea syndrome, apnea and hypopnea portions appear as a respiratory signal of low amplitudes, and subsequent labored respirations appear as a signal of high amplitudes. Therefore, a respiratory disorder pattern in which a signal of low amplitudes is followed by a signal of high amplitudes, included in a respiratory signal is extracted from a load signal. By counting the number of respiratory disorders including apneas and hypopneas, the frequency of respiratory disorders can be measured. The averaged amplitude data is suitable for excluding the influence of limb movements that produce noises. However, in patients of serious apnea syndrome, respiratory disorders occur more frequently than limb movements that produce noises. In some cases, only a signal of only one or two high amplitudes indicating forced respirations may be included in the respiratory disorder pattern. Therefore, the averaged amplitude data may make it difficult to detect such a respiratory disorder pattern. On the other hand, in patients of mild apnea syndrome, since they have plenty of sleeping in comparison with serious patients, they are often in an awake state or semi-awake state during measurement, and prone to be active in limb movements.

Therefore, this analyzing method, by a method of determining a significant respiratory disorder pattern by averaged amplitude data, temporarily counts the number of respiratory disorders from the respiratory signal (first step). Moreover, when the number of respiratory disorders per unit time is large, and the patient is determined as serious, the method re-counts the number of respiratory disorders by determining a significant disorder pattern by individual amplitude data (second step). By this method, for mild patients who are relatively active in limb movements, noises can be eliminated. On the other hand, for serious patients, even a respiratory disorder pattern including only one or two amplitudes indicating a labored respiration can be detected, so that the detection accuracy of an apnea hypopnea index of serious patients can be increased.

According to another aspect of the present invention, an analyzing apparatus includes a first counter part and a second counter part. The first counter part counts the number of respiratory disorders by a respiratory disorder pattern included in the above respiratory signal, determines a significant respiratory disorder pattern from averaged amplitude data, and counts the number of respiratory disorders. The second counter part determines, when the number of respiratory disorders per unit time counted by the first counter part is greater than a predetermined number, a significant respiratory disorder pattern from individual amplitude data, and again counts the number of respiratory disorders. The analyzing apparatus can be realized using a general-purpose computer that includes proper hardware resources.

According to a further aspect of the present invention, a program and a program produce are provided for instructing a computer to analyze the above respiratory signal. The analyzing processing includes a storing step, a first step and a second step. The storing step stores a respiratory signal extracted from a load signal in a memory. The first step counts the number of respiratory disorders by a respiratory disorder pattern included in the respiratory signal stored in the memory, determines a significant respiratory disorder pattern by averaged amplitude data, and counts the number of respiratory disorders. The second step determines, when the number of respiratory disorders per unit time counted previously is greater than a predetermined number, a significant respiratory disorder pattern by individual amplitude data stored in the memory, and again counts the number of respiratory disorders. The program or program product can be delivered in a form recorded in a suitable recording medium such as CD-ROM, and can be delivered via a computer network such as the Internet.

Preferably, the second step and the second counter part set the amplitude ratio of a signal of high amplitudes to a signal of low amplitudes included in the significant respiratory disorder pattern lower than the amplitude ratio of the significant respiratory disorder pattern in the first step and the first counter part. The detection sensitivity of respiratory disorders for respiratory signals of serious patients can be further increased.

When the second step and the second counter part determine that respiratory disorder patterns are included successively at a higher ratio than the specification from the individual amplitude data, it is desirable to determine a significant respiratory disorder pattern by the individual amplitude data. A relation is found between a case where a labored respiration of only one or two amplitudes is included in a respiratory disorder pattern and a case where respiratory disorder patterns appear successively as in serious patients. It is desirable therefore to count such a respiratory disorder pattern without eliminating it as noise. The continuity of a respiratory disorder pattern can be determined from a high frequency of regular respiratory disorder patterns. For example, the interval and the standard deviation of maximum peaks included in individual amplitude data per unit time are obtained, and the ratio of continuous respiratory disorder patterns can be determined by a value produced by dividing the standard deviation by the average. To determine whether maximum peaks were caused by a labored respiration, it is effective to add the condition that the values of maximum peaks are equal to or greater than a certain value.

Furthermore, when the first step and the counter part determine that a signal indicating an awake state is included in a load signal, it is desirable to increase the amplitude ratio of a signal of high amplitudes to a signal of low amplitudes included in a significant respiratory disorder pattern. Since mild patients often have plenty of sleep, they are probably in an awake state or semi-awake state during measurement. In the awake state, noises by body movements other than respirations may often be included in a respiration signal. By eliminating the noises, the accuracy of determining respiratory disorders can be increased.

The presence or absence of body movements other than respirations can be determined based on a difference in frequency bands and a difference in pressure sensitive elements from a load signal. The probability of being awake can be determined from a ratio of body movement time. Therefore, when information about body movements indicating the presence or absence of a subject's body movements is included in the load signal, the first step can determine that the subject is probably awake when the ratio of time for which the subject is determined to be moving his (or her) body exceeds a predetermined value.

The first step can determine that the subject is probably awake when the number of peaks (PLM) having amplitudes twice or more higher than the amplitudes of preceding and following peaks, included in the individual amplitude data (respiratory signal) of predetermined time, exceeds a predetermined value.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

Figure 1:
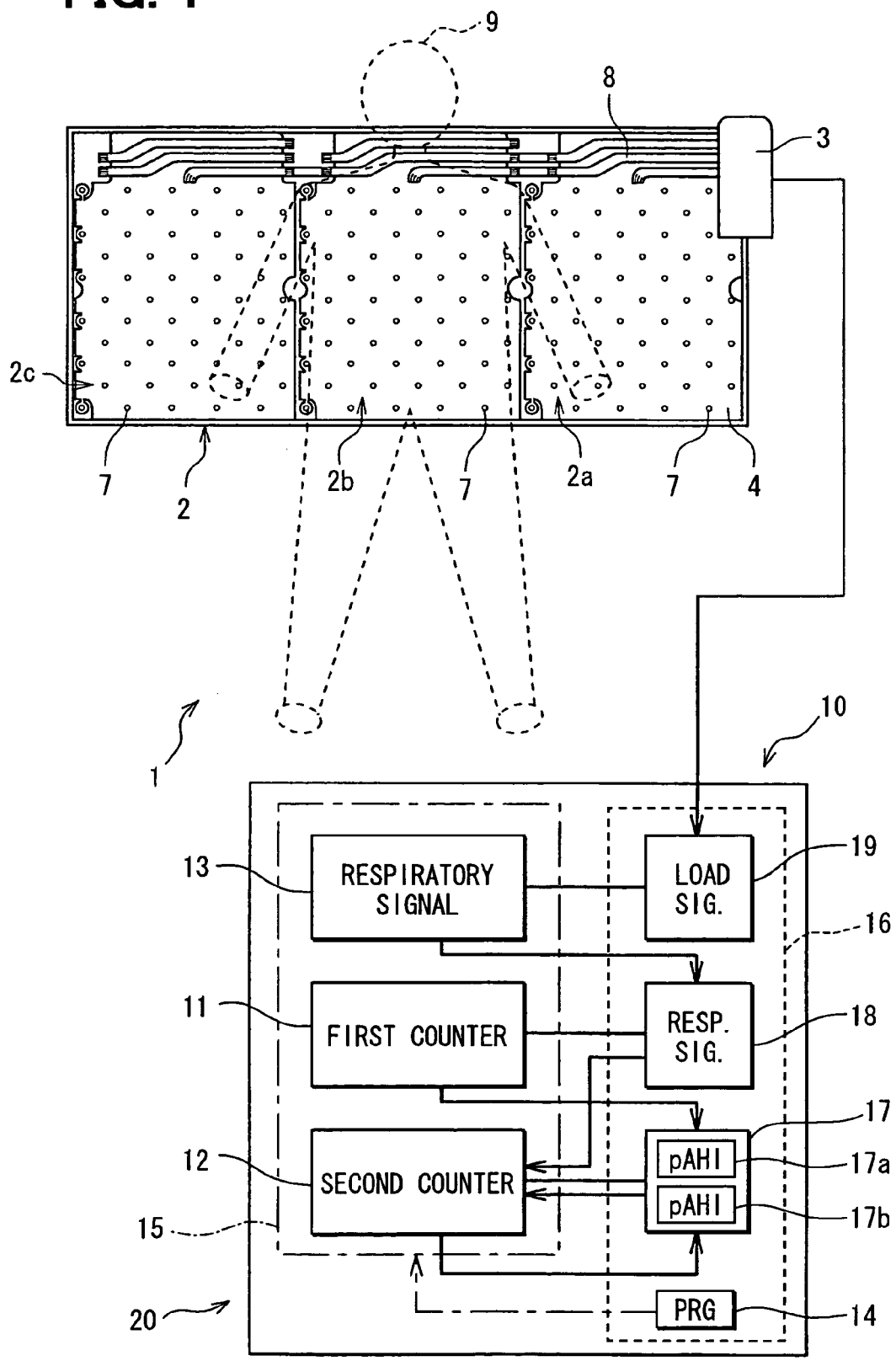
FIG. 1 is a schematic diagram showing a living body information detection system that captures changes in loads applied to a subject's bed by a sensor sheet having multiple pressure sensitive elements.

A living body information detection system shown in FIG. 1 is described as a system to determine apnea conditions of patients of the sleep apnea syndrome. The living body information detection system includes: a sensor sheet 2 on which multiple pressure sensors (pressure sensitive sensors) 7 as pressure sensitive elements are arrayed; and a control unit 3 that outputs signals from the multiple pressure sensitive sensors 7 to an analyzing apparatus 10. The sensor sheet 2 includes multiple subsheets 2a, 2b and 2c. The subsheets 2a, 2b and 2c whose base material is a thin plastic sheet 4 allow the multiple pressure sensitive sensors 7 mounted on the sheet 4 to be regularly disposed in an appropriate interval. The sheet 4 has a wiring 8 for outputting signals from the multiple pressure sensitive sensors 7. Therefore, by placing the sensor sheet 2 on a bed or the like, numerous pressure sensitive sensors 7 can be placed on the bed. Without having to attach the pressure sensitive sensors 7 directly to a subject 9 such as a patient lying on the bed, a body movement of the subject 9 can be converted into a signal (load signal) from the pressure sensitive sensors 7 as a change of loads applied to the bed. Therefore, by analyzing the load signal from the pressure sensitive sensors 7, respiratory conditions and other conditions of the subject during sleeping can be monitored.

The analyzing apparatus 10 includes a computer 20 having proper hardware resources. The computer 20 includes, for example, a memory 16 for storing data and programs, and a CPU 15 that downloads programs to perform processing. The memory 16 is a recording medium capable of input and output, for example, a hard disk or semiconductor memory.

The memory 16 includes; a load signal storage area 19 that stores the load signal applied from the control unit 3, a respiratory signal storage area 18 that stores a respiratory signal; an apnea hypopnea index storage area 17 that stores the apnea hypopnea index; and an analyzing program storage area 14 that stores the analyzing program 14. The apnea hypopnea index storage area 17 further includes a first area 17a that stores a first-time pAHI, and a second area 17b that stores a second-time pAHI, which respectively store counted numbers.

The load signal obtained by the sensor sheet 2 is temporarily stored in the memory 16 of the analyzing apparatus 10. The load signal is analyzed on time in the case of monitoring the conditions of a patient as the subject 9 according to the presence or absence of respiration and the presence or absence of body movement. In examination of the apnea syndrome, on-time analysis is not usually required, but is performed collectively when sleeping data has been collected completely or to some extent.

The computer 20 functions as the analyzing apparatus 10 by an analyzing program 14 stored in the memory 16. The analyzing apparatus 10 has a respiratory signal producing part 13 that extracts the respiratory signal from the signal and stores it in the memory 16, a function as a first counter part that analyzes the respiratory signal in a first condition (determines a significant respiratory disorder pattern by averaged amplitude data forming an average of multiple amplitudes contained in the respiratory signal), counts an apnea hypopnea index (pAHI), and outputs it to the memory 16, and a function as a second counter part 12 that, if the subject is determined as a serious patient from the result of pAHI obtained in the first condition, analyzes the respiratory signal in a different condition and recounts second pAHI.

The first counter part 11 corresponds to a first respiratory disorder number count means, and the second counter part 12 corresponds to a second respiratory disorder number count means. The first and the second counter parts 11 and 12 are respectively constructed as control parts, for example. The control parts respectively include counters, which count the number of respiratory disorders.

Throughout this disclosure, the terms "peak" or "peaks" will be used to describe the crest or crests (i.e., points of maximum amplitude) of the respiratory disorder pattern 85.

The first counter part 11, for each of peaks forming a respiratory disorder pattern 85 (FIG. 5C), determines the average of maximum values of multiple peaks including the peak from individual amplitude data, creates an averaged amplitude pattern 86 constituted from the determined averages, and counts as the number of respiratory disorders a number of amplitudes of the averaged amplitude pattern 86 per unit time that exceed a reference value used to evaluate the sleep apnea syndrome.

When the number of respiratory disorders counted in the first counter part 11 is a number indicating the sleep apnea syndrome, the second counter part 12 determines whether maximum values of peaks of the respiratory disorder pattern 85 appear successively in the individual amplitude data. When maximum values of peaks of the respiratory disorder pattern 85 appear successively, it reduces the reference value that is used to evaluate amplitudes of the averaged amplitude pattern 86 per unit time for the sleep apnea syndrome, and counts the reduced value as the new number of respiratory disorders.

Figure 2:
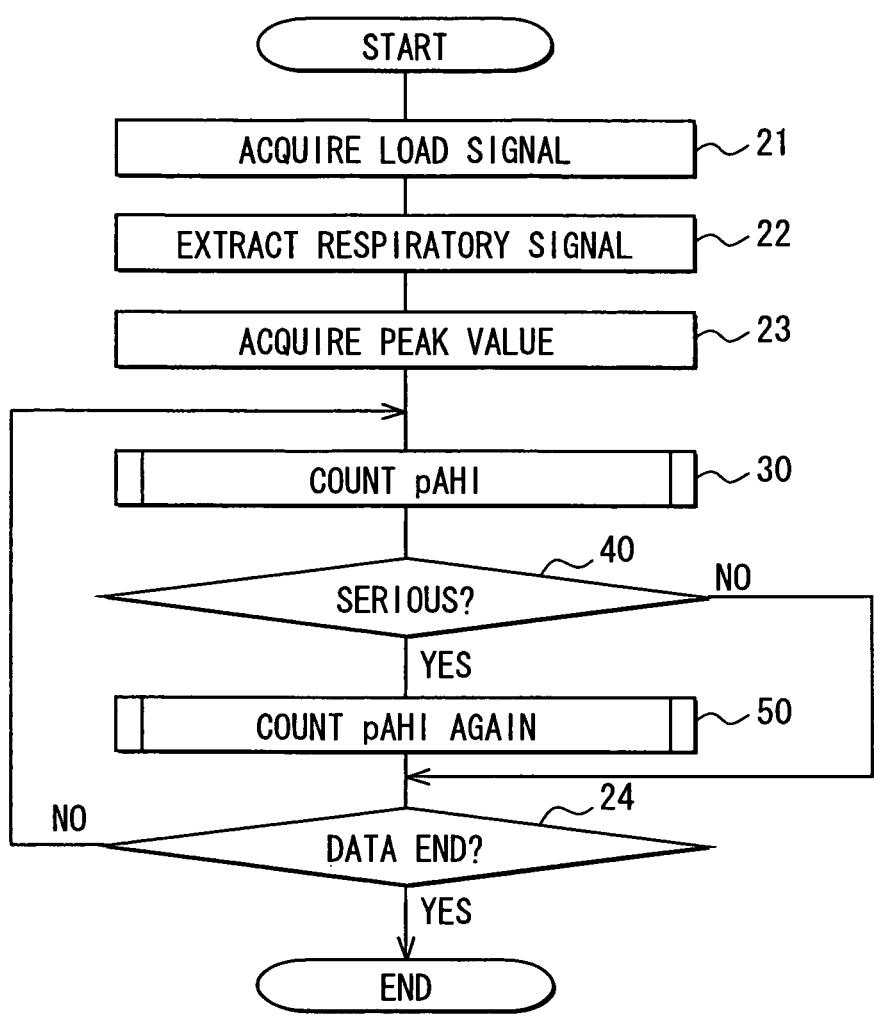
FIG. 2 is a flowchart showing pAHI counting processing in an analyzing apparatus of the living body information detection system.

The analyzing apparatus 10 performs the apnea syndrome examination processing as shown in FIG. 2. The analyzing apparatus 10 produces the respiratory signal for analysis by the respiratory signal producing part 13. For this reason, in step 21, it acquires the load signal of the subject 9 by the sensor sheet 2. In step 22, it extracts a signal component of a frequency band corresponding to a respiratory rate of the subject 9 as the respiratory signal, using a method such as Fast Fourier Transform (FFT). Furthermore, in step 23, it acquires the peak value (data) of the respiratory signal, and stores it in the memory 16 as the respiratory signal for analysis. Processing for producing the respiratory signal may be performed in other analyzing apparatuses or the control unit 3 of the sensor sheet. In this case, the produced respiratory signal for analysis is supplied to the memory 16 together with other information via a proper recording medium or LAN.

Figure 5A:
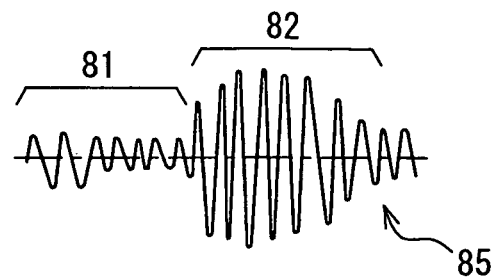
FIGS. 5A, 5B, 5C and 5D are signal waveforms showing typical respiratory disorder patterns included in a respiratory signal and several states in the process of analyzing the respiratory signal.
Figure 5B:
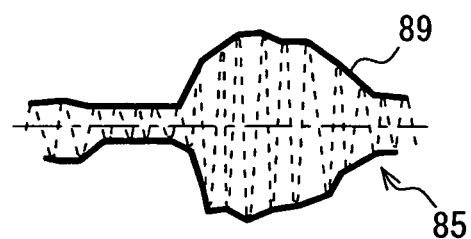

FIG. 5A shows a typical example of the respiratory signal. A signal included in the signal as a respiratory body movement is caused by a respiratory body movement, such as a vertical movement of a chest area, and pulsates at an almost constant cycle. The respiratory signal of the subject 9 having the apnea syndrome, which is not constant in the amplitude of pulsation, has a respiratory disorder pattern 85 in which a signal 81 of low amplitudes (signal of first amplitudes) is followed by a signal 82 of high amplitudes (signal of second amplitudes). Therefore, in step 23, the analyzing apparatus 10 extracts data of each peak (amplitude and time or cycle) of the pulsating signal. As a result, data corresponding to an amplitude envelope 89 is extracted as shown by a solid line in FIG. 5B. Hereinafter, a collection of the values of the peak value is handled as the respiratory signal (respiration data, individual amplitude data).

After the production of the respiratory signal or concurrently with the production, in this example, the respiratory signal is analyzed every five minutes to obtain pAHI. Specifically, in step 30, the first counter part 11 of the analyzing apparatus 10 analyzes a five-minute respiratory signal stored in the memory 16, counts the first-time pAHI, and outputs the result to the memory 16. When determining in step 40 that the patient is serious from the value of the first-time pAHI. In step 50, the second counter part 12 changes the conditions of determining a respiratory disorder to analyze the respiratory signal stored in the memory 16, and counts the second-time pAHI. These processes are repeated until data comes to an end in step 24.

Figure 3:
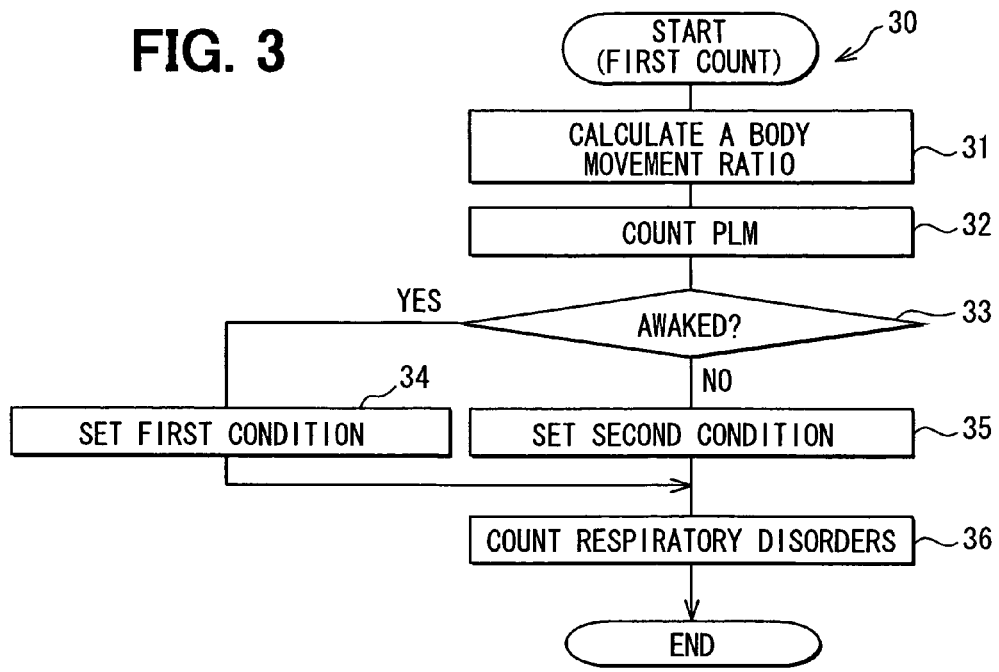
FIG. 3 is a flowchart showing first-time pAHI counting processing in the analyzing apparatus.

The processing (first process) 30 that counts the first-time pAHI in the first counter part 11 is described with reference to FIG. 3. In step 31, the first counter part 11 calculates a body movement ratio of five minutes, which are an analysis target period. The body movement ratio is defined as a ratio (%) of body movement time (time for which the subject 9 is determined to be moving his (her) body) to the target period (five minutes). Body movements in this phase are body movements of the subject 9 on the bed which are differentiated from respiratory body movements. The presence or absence of such body movements is determined from the signal. If the positions of the pressure sensors 7 on which the subject 9 are determined to be lying in a predetermined interval (25.6 seconds in this example) change 70% or more, it is determined that the subject 9 is moving his (her) body.

In step 32, the first counter part 11 counts PLM included in the five-minute respiratory signal. PLM indicates a single-shot peak included in the respiratory signal. When the amplitude of a peak included in the respiratory signal is twice or more the amplitudes of a preceding peak and a following peak, the peak is determined as PLM and counted.

In step 33, the first counter part 11 determines whether the probability the subject 9 is awake is high, from the body movement ratio and the number of PLMs. The sleep apnea syndrome (SAS) refers to cases where apneas of 10 seconds or more are recognized 30 times or more during sleep (seven hours) of a single night, or five times or more in average to an hour. Some of them are recognized even during sleeping in an awake state in terms of brain waves. Therefore, although it is required to determine the presence or absence of a respiratory disorder even in an awake state in terms of brain waves, body movements other than respiration are often recognized in the awake state in terms of electroencephalogram, and provisions are required to eliminate noises generated by them.

In this example, when the body movement ratio is 35% or more, or the number of PLMs is eight or more, they are regarded as signals indicating the probability of being awake. It is determined that the probability the subject 9 is awake is high. Furthermore, also when the body movement ratio is 25% or more, and the number of PLMs is four or more, it is determined that the probability the subject 9 is awake is high. These determination conditions are determined by comparing the signal with a body movement ratio and the number of PLMs when determined as an awake state in a sleeping stage in PSG.

In a case where the probability of being awake is high, it is determined that many noises due to body movements other than respiration operation are included in the respiratory signal. In step 34, the first counter part 11 sets a first condition to determine a respiratory disorder in severe conditions. In other cases, in step 35, the first counter part 11 sets a second condition milder than the first condition.

In step 36, the first counter part 11 analyzes the respiratory signal according to the set conditions, counts the number of respiratory disorder, and obtains first-time pAHI. In step 36, it creates a pattern (averaged amplitude data) forming the average of multiple amplitudes included in the respiratory signal, after the pattern is added with the condition set in step 34 or step 35, determines whether the pattern corresponds to a significant respiratory disorder pattern, and counts the number of respiratory disorders. In this example, for a peak of the respiratory signal, the first counter part 11 obtains the average of the amplitude of the peak and the amplitudes of three preceding peaks, and obtains as averaged amplitude data 86 a four-amplitude envelope, which is a pattern formed by the averages.

Figure 5C:
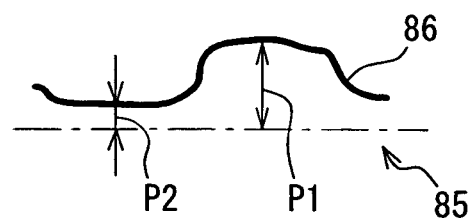
Figure 5D:
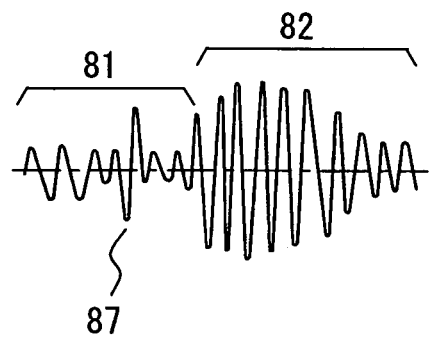

In FIG. 5C, a four-amplitude envelope 86 is shown as an example of averaged amplitude data 86. A method of averaging peaks is not limited to this; three amplitudes, or five amplitudes or more may be averaged. By forming the pattern 86 forming the averages of multiple amplitudes, a single-shot peak 87 shown in FIG. 5D will hardly appear in the pattern 86 as a result of averaging. Therefore, without influence of noise due to periodic limb movements, the presence or absence of a significant respiratory disorder pattern can be determined by the number of peaks to be averaged. Although the influence of single-shot peaks can be prevented, the respiratory disorder pattern tends to dull. Therefore, as the respiratory pattern 86 for counting the first-time pAHI, it is desirable to adopt averaged amplitude data 86 of three amplitude or four amplitudes instead of an original respiratory signal (individual amplitude data).

The first and second conditions (that is, reference values used to evaluate the sleep apnea syndrome) respectively set in steps 34 and 35 include an amplitude ratio and the need for actual amplitude determination. An amplitude ratio PR is the ratio of a maximum value P1 of the averaged amplitude pattern 86 to a preceding minimum value P2. The first condition dictates that the amplitude ratio PR is 2.0 times or more, and the second condition dictates that the amplitude ratio PR is 1.6 times or more. Accordingly, in a state in which the second condition has been set, in step 36, the pattern 86 having an amplitude ratio PR of 1.6 times or more is counted as a significant respiratory disorder pattern.

Furthermore, the first and second conditions require that actual amplitude determination is made. In the actual amplitude determination, the actual values of four peaks contributing to the minimum value P2 are compared with the maximum value P1, and it is determined whether the values of at least two of the four peaks satisfy the condition of the amplitude ratio PR. A case where the minimum value P2 is formed by one or two peaks having extremely small amplitudes can be excluded as noise.

Besides, on the premise that the respiratory disorder pattern occurs periodically, noise can be eliminated by defining a time interval between the maximum value P1 and the minimum value P2. A condition of a frequency (cycle) of pulsation giving the maximum value P1 and the minimum value P2 can be added to determine a significant respiratory disorder pattern.

As shown in FIG. 2, in step 40, the analyzing apparatus 10 determines whether the subject 9 is serious, from the first-time pAHI. In the sleep apnea syndrome, when AHI per hour is less than 20, from 20 to 30, from 31 to 50, and 51 or more, the case is defined as mild, moderate, serious, and critical, respectively. Critical patients are awake every almost one minute or less, often in a very dangerous state. Therefore, it is important as examination of the sleep apnea syndrome to determine whether the subject 9 is a critical patient or not. Accordingly, in step 40, the analyzing apparatus 10 determines whether the value of the first-time pAHI counted for five minutes corresponds to 50 times per hour. If the value of the first-time pAHI is 50 times or more, in step 50, it counts the second-time pAHI.

Figure 4:
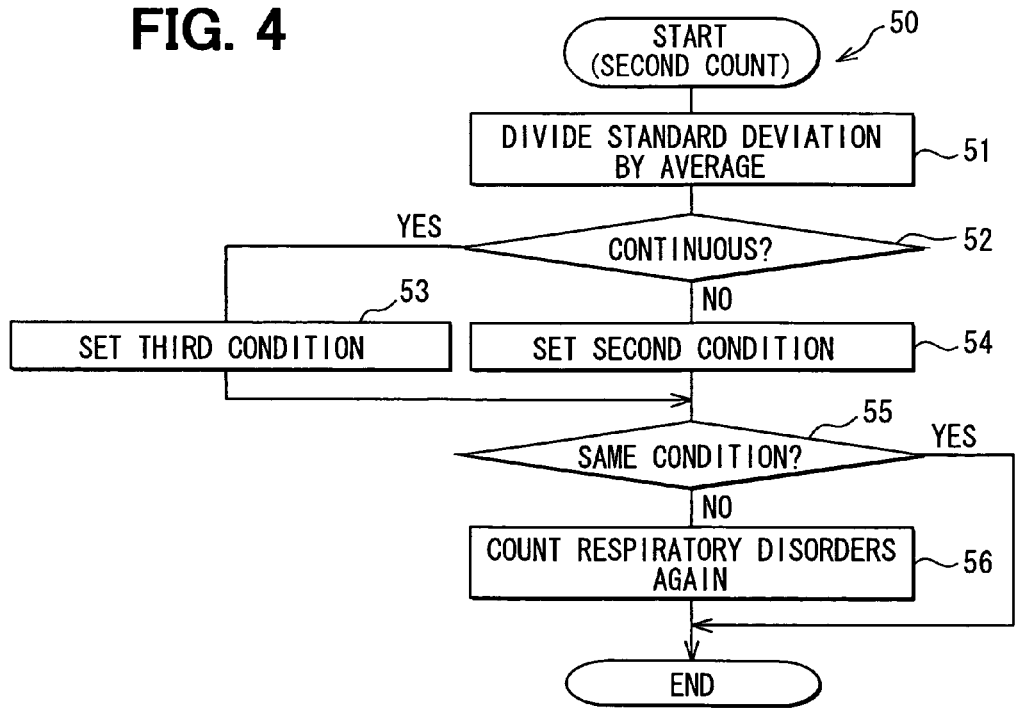
FIG. 4 is a flowchart showing second-time pAHI counting processing in the analyzing apparatus.

The processing (second process) that counts the second-time pAHI in the second counter part 12 is described with reference to FIG. 4. In step 51, the second counter part 12 determines the continuity of respiratory disorders from the actual respiratory signal, that is, the individual amplitude data. In this example, using five-minute individual amplitude data as a target, the second counter part 12, for a given maximum value, obtains the standard deviation and the average of the intervals (eight intervals) of nine preceding maximum values, and obtains a value A by dividing the standard deviation by the average. If five or more maximum values of 1.8 or less as the value A are included in the five-minute individual amplitude data (that is, larger than a prescribed value indicating the probability of the sleep apnea syndrome), the second counter part 12 determines that respiratory disorder patterns is included successively at a higher ratio than the specification in a range of the unit time, and counts the number of significant respiratory disorder patterns by the individual amplitude data. Furthermore, to confirm that the maximum values are components indicating labored respiration, maximum values that are not sufficiently large are omitted from the statistical computation.

Critical patients may develop a respiratory disorder pattern in which a labored respiration of only one or two amplitudes appear. Often, such respiratory disorder pattern appears successively. Therefore, in determination from the averaged amplitude data, such labored respiration is probably not determined as a significant respiratory disorder pattern because its amplitudes are averaged with the amplitudes of preceding or following apnea or hypopnea. If it appears successively, the pAHI is counted to a low value. It is difficult to directly determine whether only one or two high amplitudes indicate labored respiration or noise. However, for serious patients developing such a special respiratory disorder pattern, by noting that the respiratory disorder pattern is continuous, the probability of counting significant respiratory disorder patterns with a minimum of noise influence can be increased by counting respiratory disorder patterns having a small number of amplitudes indicating labored respiration.

Therefore, in the second-time counting, when the second counter part 12 determines in step 52 that the individual amplitude data 18 has continuity, it sets a third condition in step 53. The third condition dictates that it is determined whether a significant respiratory disorder pattern is included in the individual amplitude data forming the values of amplitudes of an actual respiratory signal, which are not subjected to the averaging of peak values. Furthermore, the third condition dictates that the ratio PR between the maximum value P1 and the minimum value P2 is set to 1.5, which is lower than in the second condition. When the presence or absence of a respiratory disorder pattern is determined, since multiple amplitudes are not averaged, actual amplitude determination included in other conditions is not made.

On the other hand, when it is determined in step 52 that pAHI is high but the continuity of the individual amplitude data is not so large, the analyzing apparatus 10 sets the above second condition in step 54. When it is determined in step 55 that a condition different from the first-time count in step 36 has been set, in step 56, the analyzing apparatus 10 analyzes the individual amplitude data of the memory 16 in the new condition, and outputs the re-counted second-time pAHI to the memory 16.

In this way, the analyzing apparatus 10 can determine the pAHI from the respiratory signal obtained by the sensor sheet 2. Furthermore, when the value of the first-time pAHI is large, the analyzing apparatus 10 counts the second-time pAHI in a different condition, and thereby can obtain appropriate pAHI for both serious patients and mild patients. Particularly, for critical patients having a large value of pAHI, highly accurate pAHI is obtained. Accordingly, by analyzing a respiratory signal using the analyzing apparatus 10, the accuracy of determining a patient's seriousness can be increased, and the analyzing apparatus 10 can provide satisfactory functions as the screening of PSG. That is, for patients of mild respiratory disorders, the order of examination by unnecessary PSG can be avoided, and for patients of serious respiratory disorders, detailed examination by PSG can be ordered. Furthermore, this inspection method allows pAHI to be measured in more simply and with fewer burdens on patients in comparison with PSG. Furthermore, continued monitoring is also possible. Therefore, combined use with PSG provides higher level treatment and care for patients.

The above determination values and conditions are examples, and are appropriately determined depending on the specifications of the sensor sheet 2, and the conditions of measuring the signal.

What is claimed is:

1. An analyzing method of analyzing a load signal corresponding to changes in loads of a subject applied to a bed, the load signal including a first alternating current (AC) signal having first amplitudes contained in a first width and a second AC signal having second amplitudes contained in a second width larger than the first width, the analyzing method comprising:
a first operation, performed by a first counter, including
extracting a respiratory disorder pattern in which the first AC signal is followed by the second AC signal,
extracting as a respiratory signal individual amplitude data of the amplitude values of individual crests in the respiratory disorder pattern,
selecting, in succession, each of the crests forming the respiratory disorder pattern, and determining, for each selected crest, an average of amplitude values of a plurality of crests from the individual amplitude data, the selected plurality of crests including the selected crest and one or more neighboring crests,
creating an averaged amplitude pattern of the determined averages, and
counting a number of average values of the averaged amplitude pattern that exceed a first reference value used to evaluate a sleep apnea syndrome per unit time as an initial number of respiratory disorders; and
a second operation, performed by a second counter, including
determining whether the amplitudes of the crests of the respiratory disorder pattern that are above the first reference value appear successively in the individual amplitude data when the number of respiratory disorders counted in the first step group is a number that indicates the presence of the sleep apnea syndrome, and
reducing the first reference value to a second reference value when the maximum amplitudes of the crests of the respiratory disorder pattern that are above the first reference value appear successively, and
counting a number of crests that exceed the second reference value as a new number of respiratory disorders.

2. The analyzing method according to claim 1, wherein:
the second operation includes determining a standard deviation and an average of intervals of individual crest amplitudes included in the individual amplitude data per unit time, and determining from a comparison value obtained by dividing the standard deviation by the average of the crest amplitude values whether the values of the respiratory disorder pattern that are above the first threshold appear successively.

3. The analyzing method according to claim 2, wherein:
the second operation determines that the crest amplitudes of the respiratory disorder pattern that are above the first threshold appear successively when the number of crest amplitudes that are smaller than the comparison value and included in the individual amplitude data per unit time exceeds a prescribed value indicating a probability of the sleep apnea syndrome.

4. The analyzing method according to claim 1, wherein:
the first operation uses, as the first reference value, an amplitude ratio between the maximum value of the averaged amplitude pattern and a minimum value preceding the maximum value of the averaged amplitude pattern.

5. The analyzing method according to claim 1, wherein:
the first operation includes determining whether a signal indicating a probability that the subject is awake is included in the load signal, and sets the first reference value to a first number when it is determined that the subject is awake, and sets the first reference value to a second number when it is determined that the subject is not awake, the first number being larger than the second number.

6. The analyzing method according to claim 5, wherein:
the load signal includes a signal indicating a presence or absence of body movements of the subject; and
the first operation determines that the subject is probably awake when time for which the subject is considered to be moving his/her body exceeds a time for which the subject is considered to be awake.

7. The analyzing method according to claim 5, wherein:
the first operation determines that the subject is probably awake when the number of crests, which are included in the individual amplitude data per unit time and have amplitudes twice or more higher than amplitudes of preceding and following crests, exceeds a value indicating that the subject is awake.

8. An analyzing apparatus analyzing a load signal corresponding to changes in loads of a subject applied to a bed, the load signal including a first alternating current (AC) signal having first amplitudes contained in a first width and a second AC signal having second amplitudes contained in a second width larger than the first width, the analyzing apparatus comprising:
a means that extracts a pattern in which the first AC signal is followed by the second AC signal as a respiratory disorder pattern;
a means that extracts individual amplitude data including maximum values of individual peaks in the respiratory disorder pattern;
a first respiratory disorder counting means that, for each of the crests forming the respiratory disorder pattern,
selects, in succession, each of the crests forming the respiratory disorder pattern,
determines an average of amplitude values of a plurality of crests from individual amplitude data, the selected plurality of crests including the selected crest and one or more neighboring crests, and
creates an averaged amplitude pattern including determined averages, and counts a number of average values of the averaged amplitude pattern that exceed a first reference value used to evaluate a sleep apnea syndrome per unit time as an initial number of respiratory disorders; and
a second respiratory disorder counting means that determines whether the amplitude values of crests of the respiratory disorder pattern appear successively in the individual amplitude data when the number of respiratory disorders counted in the first respiratory disorder counting means is a number indicating the sleep apnea syndrome, and reduces the first reference value to a second reference value when the amplitude values of crests of the respiratory disorder pattern appear successively, and counts a number of amplitude values of crests that exceed the second reference value as a new number of respiratory disorders.

9. The analyzing apparatus according to claim 8, wherein:
the second respiratory disorder counting means determines a standard deviation and an average of intervals of individual crest amplitude values included in the individual amplitude data per unit time, and determines that the crest amplitude values of the respiratory disorder pattern appear successively when the number of crest amplitude values that are smaller than a value obtained by dividing the standard deviation by the average of the crest amplitude values and included in the individual amplitude data per unit time exceeds a prescribed value indicating the probability of the sleep apnea syndrome.

10. The analyzing apparatus according to claim 8, wherein:
the first respiratory disorder counting means determines whether a signal indicating the probability that the subject is awake is included in the load signal, and sets the first reference value to a first number when the subject is awake and to a second number when the subject is not awake, the first number being larger than the second number.

11. The analyzing apparatus according to claim 8, wherein:
the first respiratory disorder counting means uses, as the first reference value, an amplitude ratio between the maximum value of the averaged amplitude pattern and a minimum value of the averaged amplitude pattern preceding the maximum value.

12. A non-transitory computer-readable medium, having embodied thereon a program that analyzes a load signal corresponding to changes in loads of a subject applied to a bed, the load signal including a first alternating current (AC) signal having first amplitudes contained in a first width and a second AC signal having second amplitudes contained in a second width larger than the first width, wherein the program comprises instructions, which, when executed by a computer, comprises:
a first operation including
extracting a respiratory disorder pattern in which the first AC signal is followed by the second AC signal,
extracting individual amplitude data of the maximum values of individual crests of the respiratory disorder pattern as a respiratory signal,
selecting, in succession, each of the crests forming the respiratory disorder pattern, and determining for each selected crest, an average of amplitude values of a plurality of crests from the individual amplitude data, the selected plurality of crests including the selected crest and one or more neighboring crests,
creating an averaged amplitude pattern of the determined averages, and
counting a number of average values of the averaged amplitude that exceed a first reference value used to evaluate a sleep apnea syndrome per unit time as an initial number of respiratory disorders; and
a second operation including
determining whether the amplitudes of crests of the respiratory disorder pattern that are above the first reference value appear successively in the individual amplitude data when the number of respiratory disorders counted in the first step group is a number that indicates the presence of the sleep apnea syndrome, and reducing the first reference value to a second reference value when the values of the crests of the respiratory disorder pattern that are above the first reference value appear successively, and counting a number of crests exceeding the second reference value as a new number of respiratory disorders.

13. The program according to claim 12, wherein:

the second operation determines a standard deviation and an average of intervals of individual crest amplitude values included in the individual amplitude data per unit time, and determines from a comparison value obtained by dividing the standard deviation by the average of the crest amplitude values whether the values of the respiratory disorder pattern that are above the first reference value appear successively; and the second operation determines that the crest amplitudes of the respiratory disorder pattern that are above the first reference value appear successively when the number of crest amplitudes that are smaller than the comparison value and included in the individual amplitude data per unit time exceeds a prescribed value indicating a probability of the sleep apnea syndrome.

14. The program according to claim 12, wherein the first operation includes determining whether a signal indicating a probability that the subject is awake is included in the load signal, and setting the first reference value to a first number when it is determined that the subject is awake, and setting the first reference value to a second number when it is determined that the subject is not awake, the first number being larger than the second number.

15. The program according to claim 12, wherein:

the first operation uses, as the first reference value, an amplitude ratio between the maximum value of the averaged amplitude pattern and a minimum value preceding the maximum value of the averaged amplitude pattern.

* * * * *